US00PP11065P

United States Patent [19]

Lowe et al.

[11] Patent Number: Plant 11,065

[45] Date of Patent: Sep. 21, 1999

[54] KIWI PLANT NAMED 'TOMUA'

[76] Inventors: Russell G Lowe; Hinga D Marsh, both of The Horticulture and Food Research Institute of New Zealand Limited, Private Bag 11030, Palmerston North, New Zealand

[21] Appl. No.: 08/996,802

[22] Filed: Dec. 23, 1997

[51] Int. Cl.[6] ..... A01H 5/00

[52] U.S. Cl. ..... Plt./156

[58] Field of Search ..... Plt./33.1, 156

[56] References Cited

PUBLICATIONS

UPOV CD–ROM Kiwi plant named 'Tomua', PBR KIW009, New Zealand, May 1995.

*Primary Examiner*—Howard J. Locker
*Assistant Examiner*—Melissa L. Kimball
*Attorney, Agent, or Firm*—Quarles & Brady

[57] ABSTRACT

A new and distinct kiwi plant of the species *Actinidia deliciosa* (A.Chev.) C.F. Liang et A.R. Ferguson is described. The cultivar results from a controlled pollination of *A. deliciosa* DA02_03, a male selection of unknown parentage, and the female *A. deliciosa* 'Hayward', the most widely grown cultivar of kiwi worldwide. Both named parents (DA02_03 and 'Hayward') are unpatented cultivars. The new cultivar is distinguished by its early harvest time (about 4 weeks ahead of 'Hayward' in NZ), fruit appearance similar to 'Hayward', and moderate plant vigor.

5 Drawing Sheets

BACKGROUND TO THE INVENTION

Kiwi plants in cultivation are deciduous vines of *A. deliciosa*. There are more than 60 species in the genus Actinidia originating in China and parts of Asia. The kiwi cultivar 'Hayward', developed in New Zealand, is the most widely grown cultivar because of its distinctive green flesh, good flavor and long storage life. Plants are dioecious, so male pollinizers are required as well as female plants to ensure fruit production.

Kiwi plants grow vigorously in spring, and rapidly develop a canopy of canes up to 6 m long if not managed correctly. Plants require a mild, warm-temperate climate, free from late spring and early autumn frosts, and need well-drained soils to produce consistent, heavy crops of fruit. Regular irrigation is necessary in dry spells. Flowering occurs in late spring (mid-late November in New Zealand). The distinctive, green-fleshed fruit develop rapidly after pollination and reach 90% of their harvest weight after 3 months. Fruit from the cultivar 'Tomua' is harvested in early April in New Zealand, while 'Hayward' is normally harvested during May.

SUMMARY OF THE INVENTION

The present invention relates to a new and distinctive kiwi plant having an ovoid shaped fruit. More particularly, the new cultivar is designated 'Tomua', and is derived from a controlled pollination of *A. deliciosa* DA02_03, an unpatented male selection of unknown parentage, and 'Hayward', also unpatented. The male parent, which originated from seeds introduced from China in 1975, was selected as the pollen parent for the crosses because of its very early-flowering characteristics. The seed parent 'Hayward' was selected for its large size, good flavor and good storage life.

The new cultivar of kiwi was created in the course of a plant breeding program which was initiated in 1983 at Hort Research in Te Puke, New Zealand. An early-flowering unpatented *A. deliciosa* male, DA02_03, was crossed on to the unpatented seed parent 'Hayward' by Russell Lowe in November 1983. 59 seedlings from this cross were planted out in the field in April 1986. By December 1990 most plants had flowered and 'Tomua' was selected by Russell Lowe and Hinga Marsh from 19 female seedlings in this population. 'Tomua' fruit matured 4 weeks ahead of 'Hayward' and had acceptable fruit size, a good flavor and appeared to have commercial potential.

The new cultivar can be asexually reproduced as cuttings or by grafting or budding on to seedling or cutting-grown rootstocks of *A. deliciosa*. Trial plantings, established in 1989 at Te Puke, with plants grafted on to clonal 'Hayward' rootstocks, have shown that the unique combination of characteristics come true to form and are established and transmitted through succeeding asexual propagations. 'Tomua' flowers two weeks ahead of 'Hayward', so the usual pollinizers used for 'Hayward' are ineffective. Two new and unpatented early-flowering pollinizers designated Hortkiwi 'Ranger' and Hortkiwi 'King' have been selected as males for use in new plantings of 'Tomua'.

BRIEF DESCRIPTION OF THE ILLUSTRATIONS

Photographs of fruit on the vine were taken just prior to the harvest date. Colors may vary depending upon growing conditions under different climate, soil, and cultivation conditions and the fruit skin color may vary depending upon extent of exposure to direct sunlight.

Figure 1:
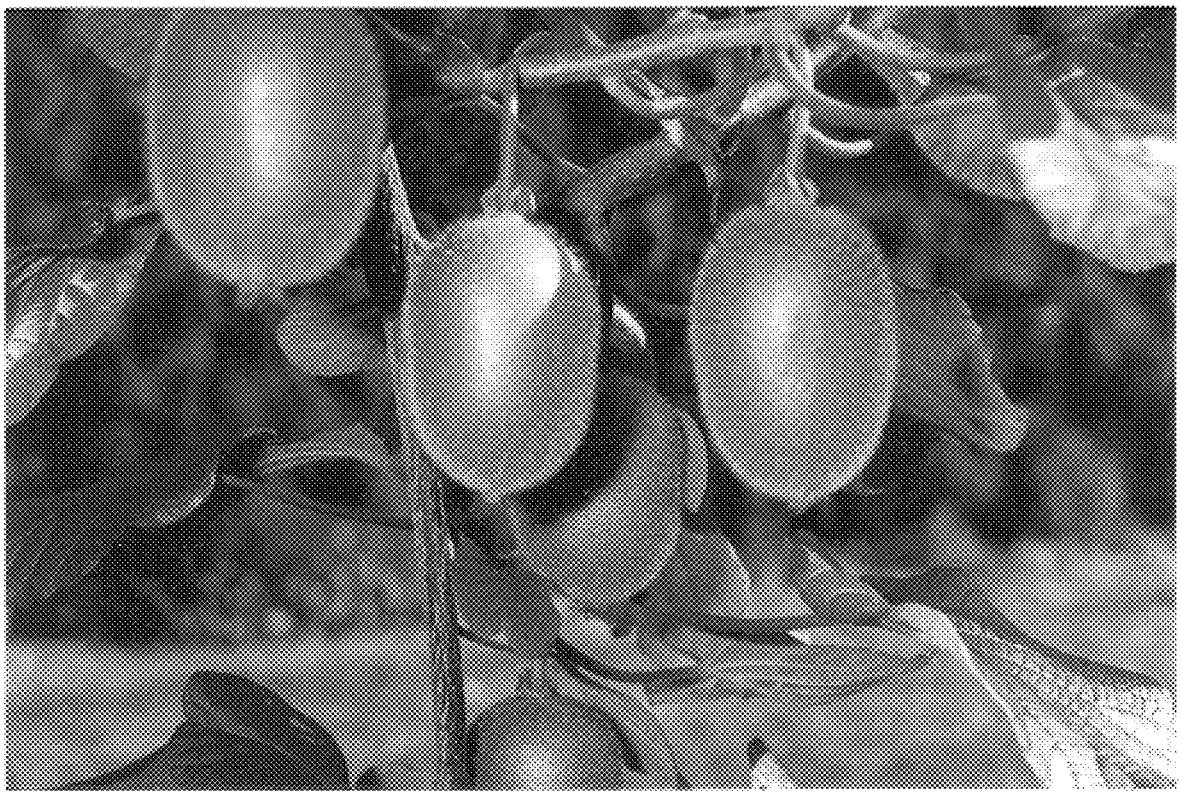
FIG. 1 shows typical fruit on the vine of the cultivar 'Tomua'.
Figure 2:
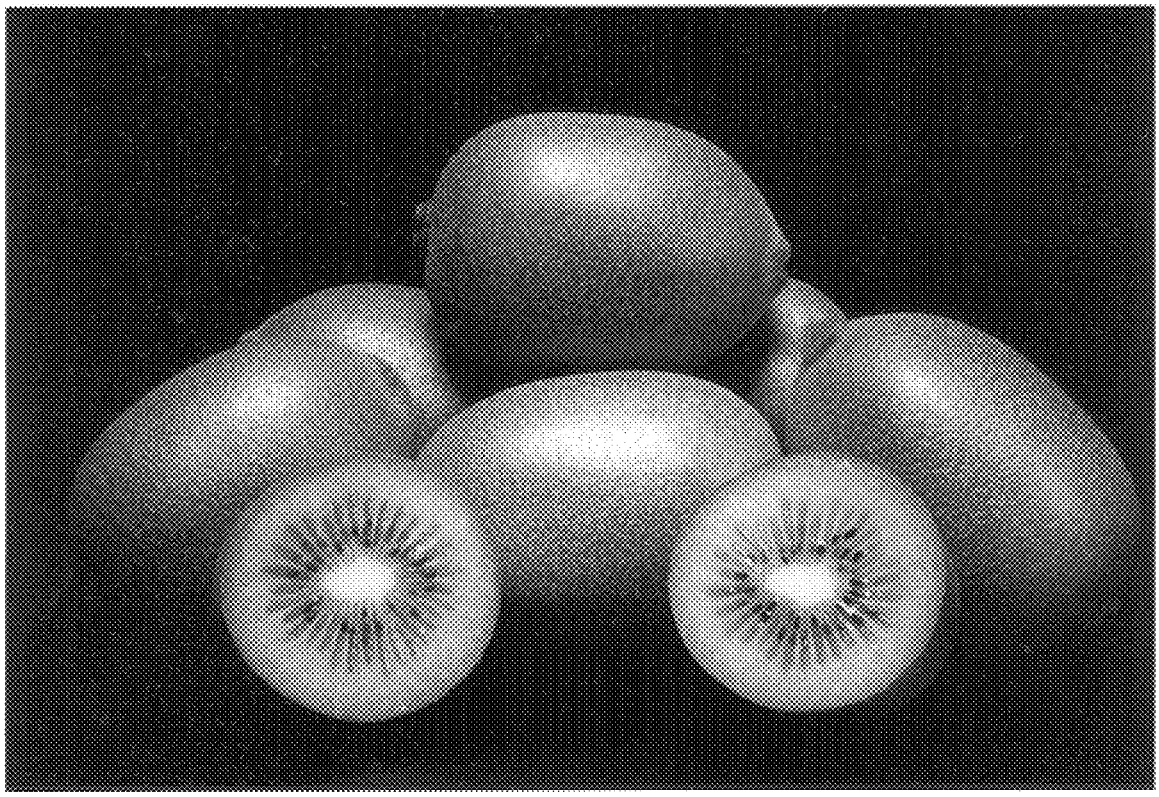
FIG. 2 shows typical fruit on the cultivar 'Tomua'. Note pointed stylar end.
Figure 3:
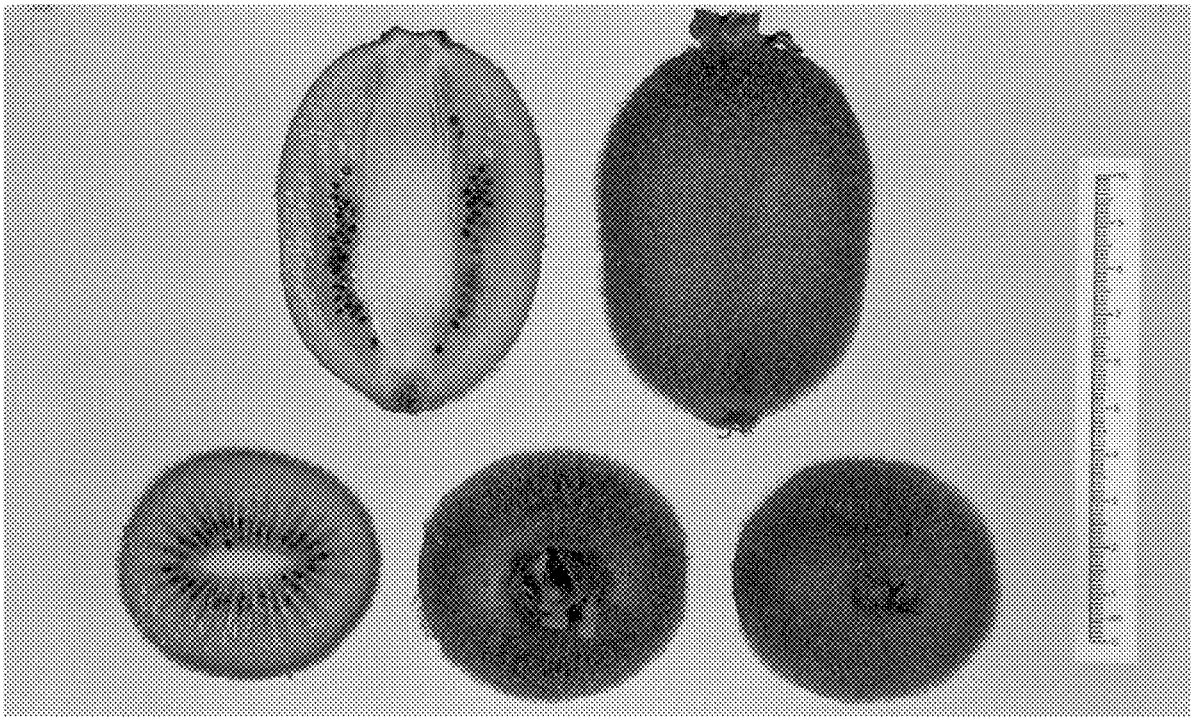
FIG. 3 shows 'Tomua' fruit in cross-section and profile.
Figure 4:
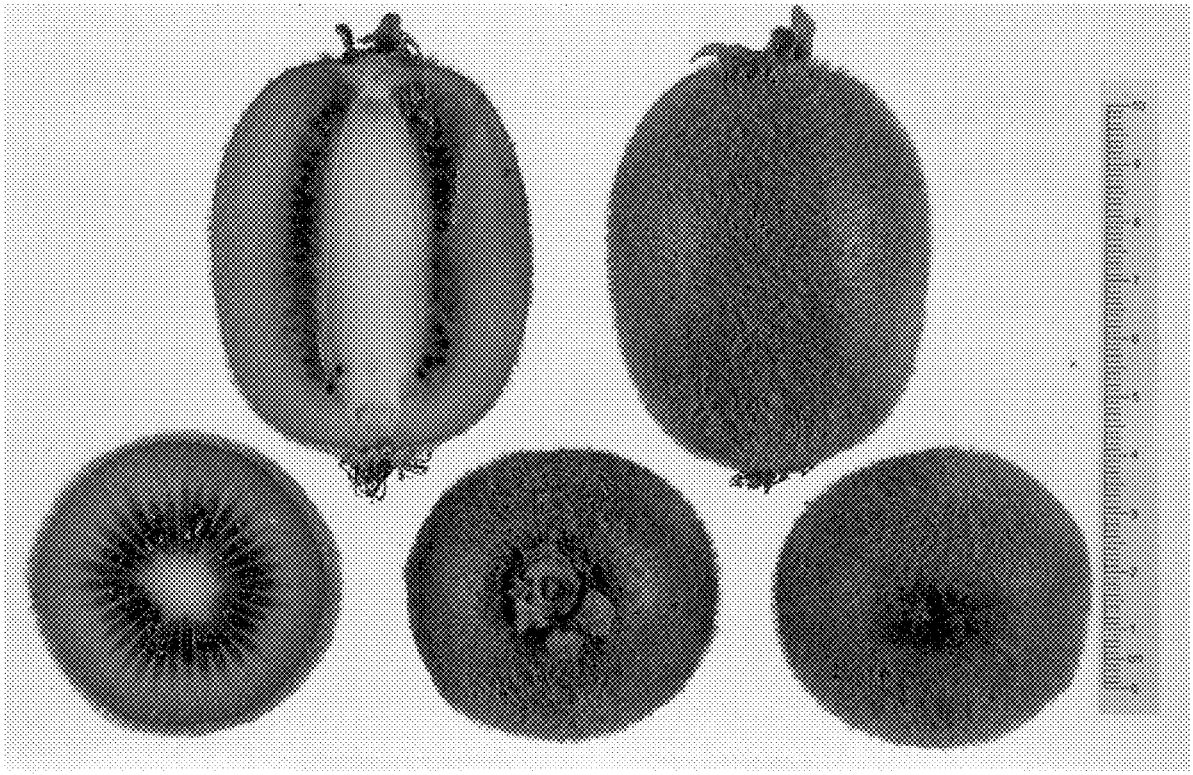
FIG. 4 shows 'Hayward' fruit in cross-section and profile.
Figure 5:
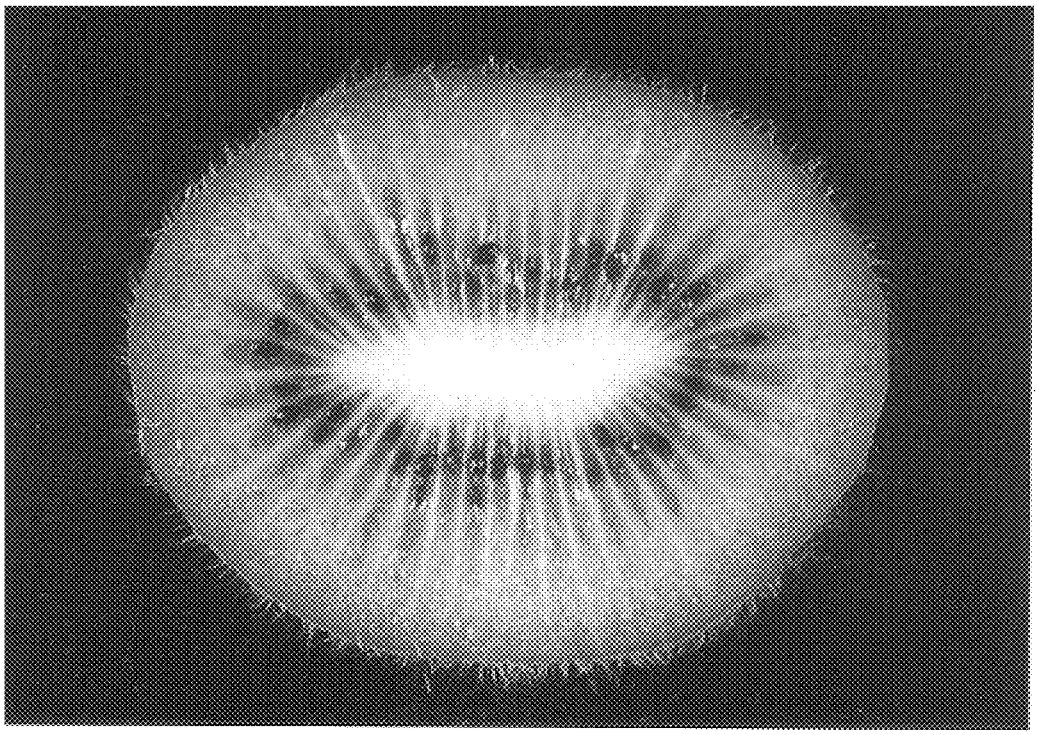
FIG. 5 shows 'Tomua' fruit in close up. Note overall similarity to 'Hayward'
Figure 6:
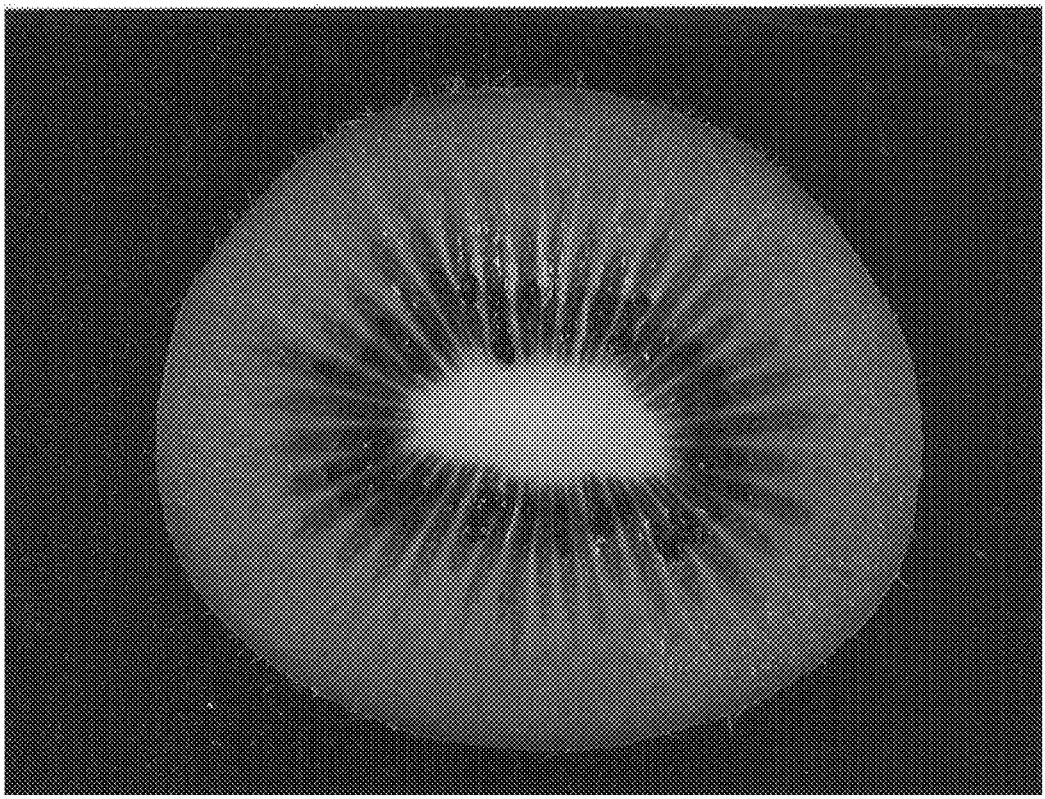
FIG. 6 shows 'Hayward' fruit in close up.
Figure 7:
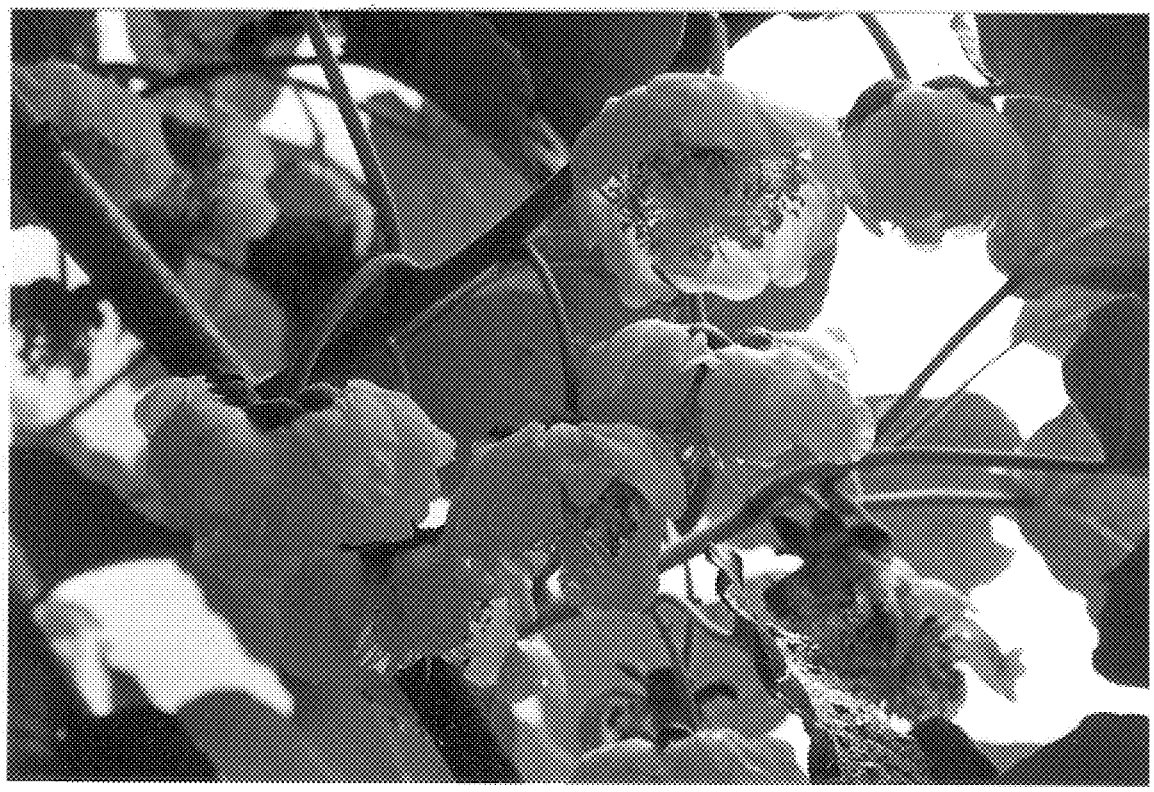
FIG. 7 shows flowers of the cultivar 'Tomua' on the vine. Note petals cupped around the ovary.
Figure 8:
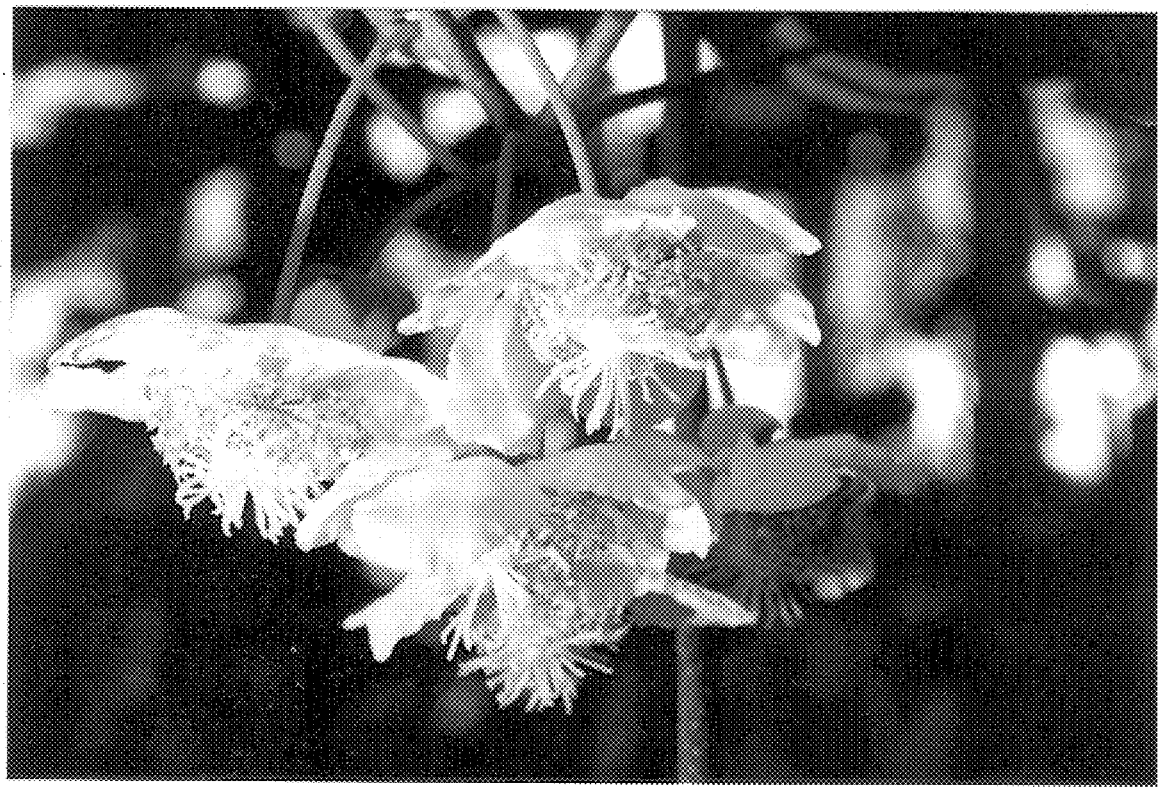
FIG. 8 shows flowers of the cultivar 'Hayward' on the vine. Note petals in horizontal alignment.
Figure 9:
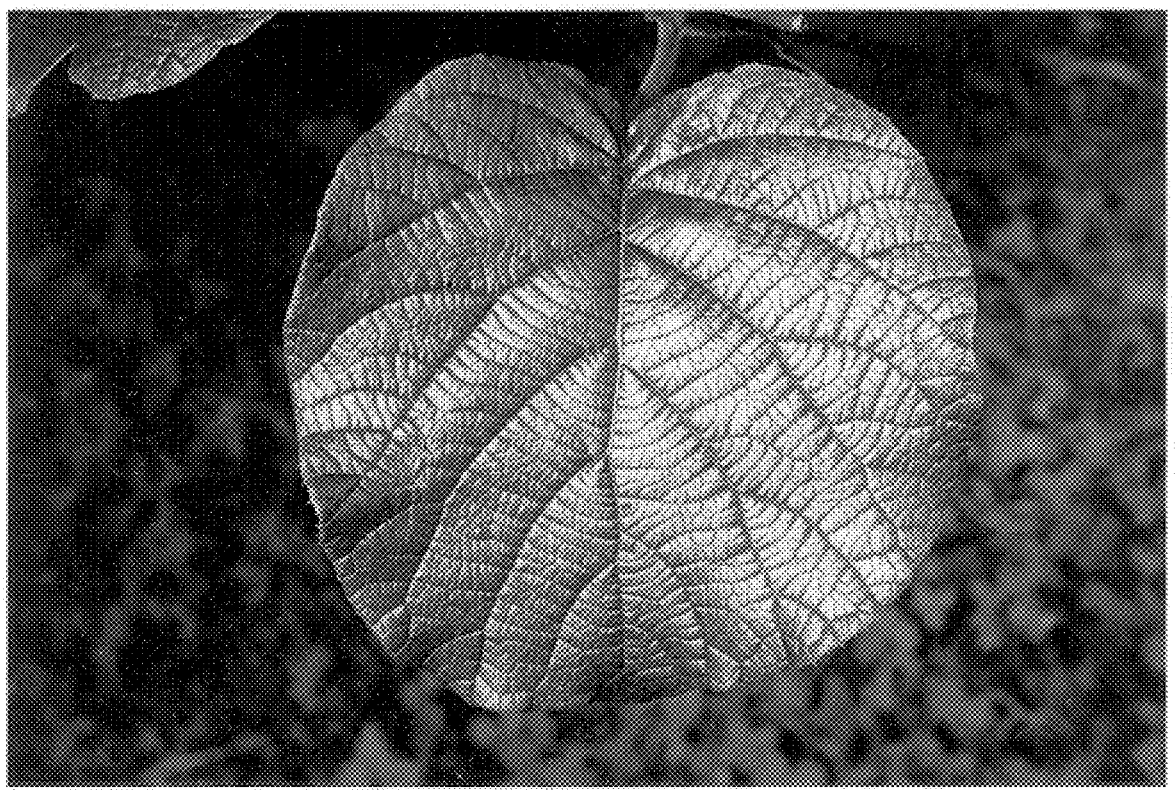
FIG. 9 shows mature leaves of the 'Tomua' vine.
Figure 10:
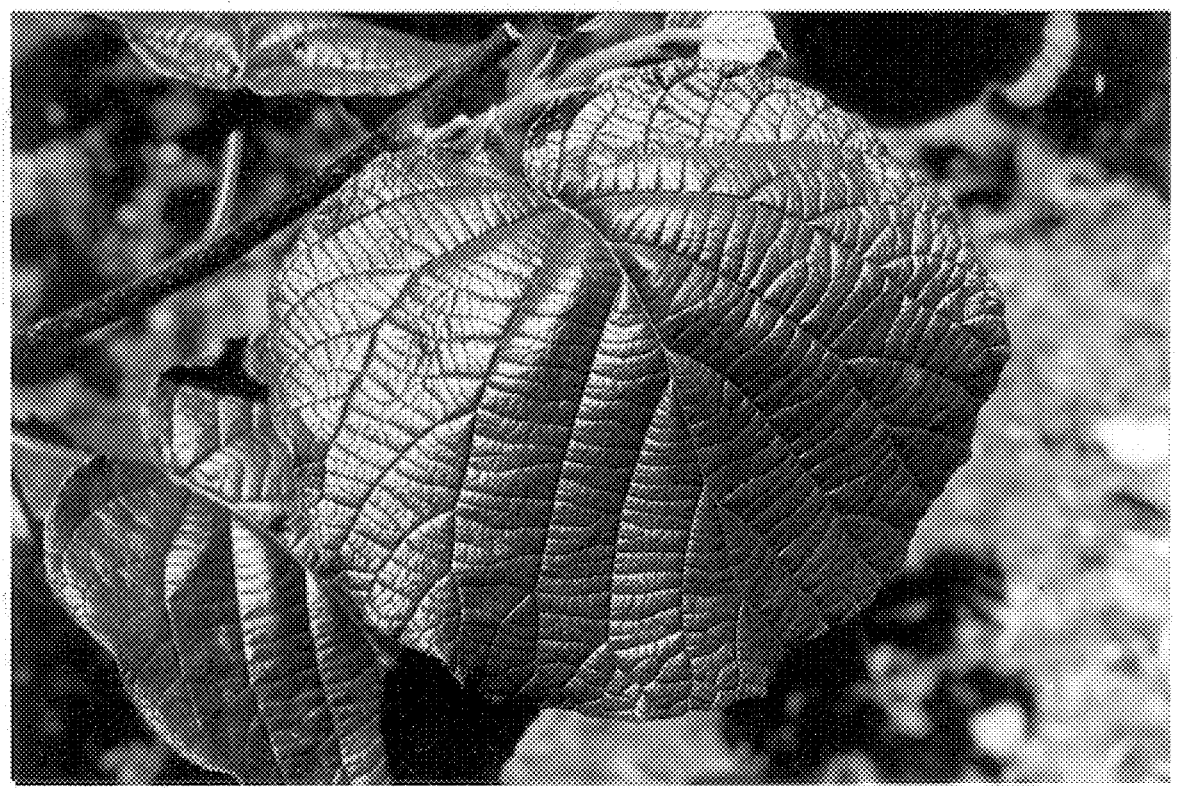
FIG. 10 shows mature leaves of the 'Hayward' vine.

The fruit of 'Tomua' are ovoid in shape, tapering towards the stylar end, generally circular in cross-section although slightly flattened (FIG. 3). The flesh of 'Tomua' fruit is medium green like 'Hayward' with a columella similar to 'Hayward' (FIG. 4). The hairs on the skin of the fruit of 'Tomua' are slightly stiffer than those of 'Hayward' and slightly prickly to the touch, but are very easily removed by rubbing or brushing to reveal a rather shiny skin (FIG. 2). The skin color of 'Tomua' fruit is a reddish-brown in contrast to that of 'Hayward' which is a medium brown color. 'Tomua' fruit are slightly longer than those of 'Hayward' for an equivalent weight. The length to (maximum) width ratio for Tomua fruit is 7:5 while that of Hayward fruit is 6:5. 'Tomua' fruit have a higher dry matter content at harvest and are sweeter tasting than 'Hayward' fruit when ripe. The storage life of 'Tomua' fruit when held at 0° C. is about 12 weeks while that of 'Hayward' is up to 25 weeks under ideal conditions.

BOTANICAL DESCRIPTION OF THE PLANT

The new cultivar 'Tomua' is pistillate with imperfect flowers, i.e., only sterile pollen is produced and thus flowers require a pollinizer for fruit production. Two specific pollinizers have been developed for 'Tomua' and they are named Hortkiwi 'Ranger' and Hortkiwi 'King'. Characteristics of the new cultivar by which it differs from the common 'Hayward' cultivar include earlier flowering and harvest times, longer fruit shape, more easily removed hairs on the skin, more pointed shape at the stylar end (FIG. 2) and reddish-brown colored skin. Horticultural terminology is used in accordance with revised UPOV guidelines for kiwi.

TABLE OF CHARACTERISITCS
Characters of the 'Hayward' comparison cultivar are noted in [bracket] opposite that character only when significantly different.
All dimensions in millimeters, weights in grams.

| | Tomua | Hayward |
|---|---|---|
| PLANT | | |
| Plant: sex expression | female | |
| Plant: ploidy | hexaploid (2n = 6x = 174) | |
| Plant: vigor | medium | |
| Young shoot: hairs | present | |
| Young shoot: density of hairs | medium | |
| Young shoot: type of hairs | velutinous | |
| Young shoot: anthocyanin coloration of growing tip | medium | |
| young shoot: anthocyanin coloration of leaf axil | weak | |
| STEM | | |
| Stem: diameter | medium - Mean 10.8 mm (Range 10.2–12.3) | |
| Stem: dormant bud diameter | 2.55 mm (1.7–3.1) | |
| Stem: color on upper side of shoot | red-brown | |
| Stem: hairs | present | |
| Stem: conspicuousness of lenticels | conspicuous | |
| Stem: number of lenticels | medium | |
| Stem: color of lenticels | brownish-white | |
| Stem: size of bud support | medium | |

-continued

TABLE OF CHARACTERISITCS
Characters of the 'Hayward' comparison cultivar are noted in [bracket] opposite that character only when significantly different.
All dimensions in millimeters, weights in grams.

| | Tomua | Hayward |
|---|---|---|
| Stem: visibility of bud (dormant canes) | inconspicuous | |
| Stem: number of hairs visible on bud (dormant canes) | few | |
| Stem: leaf scar | medium | |
| LEAF | | |
| Leaf: general shape of blade | round | [very broadly ovate] |
| Leaf: length | 140 mm (120–160 mm) | |
| Leaf: width | 149 mm (100–170 mm) | |
| Leaf: shape of tip of blade | mucronate | |
| Leaf: shape of base of blade | cordate | |
| Leaf: arrangement of leaf bases | overlapping | |
| Leaf: puckering/blistering on upper side of blade | medium | |
| Leaf: margin | ciliate | |
| Leaf: green color of upper side of blade | medium | |
| Leaf: glossiness of upper surface of blade | medium | |
| Leaf: color of lower side of blade | light green | |
| Leaf: glaucousness (lower side of blade) | absent | |
| Leaf: petiole length | 87 mm (52–150 mm) | |
| Leaf: hears on petiole | present | |
| Leaf: density of hairs on petiole | medium | |
| Leaf: anthocyanin coloration on upper side of petiole | weak | [medium] |
| FLOWER (Measurements taken from a sample of 20 flowers) | | |
| Inflorescence: predominant number of flowers | one | |
| Pedicel: length | medium - 36.9 mm (31.0–43.0 mm) | |
| Pedicel: hairs | present | |
| Pedicel: length of hairs | medium | |
| Flower: number of sepals | >5 | |
| Flower: color of sepals | brown | |
| Flower: diameter (terminal or king flower when fully open) | large - 63.3 mm (47.8–70.6 mm) | |
| Flower: petal length | 30.0 mm (25.3–34.3 mm) | |
| Flower: petal width | 22.7 mm (18.5–29.6 mm) | |
| Flower: petal length/width ratio | 1.33 mm (1.11–1.48 mm) | |
| Flower: mean number of petals per flower | 7 (6–8) | |
| Flower: number of flowers with more than six petals | 15 out of 20 flowers | |
| Flower: arrangement of petals | overlapping | |
| Flower: petal shoulder | present | |
| Flower: primary color of petals on upper side (when fully open) | white | |
| Flower: type of coloration | uniform color, | |

-continued

TABLE OF CHARACTERISITCS
Characters of the 'Hayward' comparison cultivar are noted in [bracket] opposite that character only when significantly different.
All dimensions in millimeters, weights in grams.

| | Tomua | Hayward |
|---|---|---|
| of petals | i.e., not bi-colored | |
| Flower: number of styles | 37.3 (31–43) | |
| Flower: attitude of styles | semi-erect | |
| Flower: amount of hair on ovary | strongly expressed | |
| FRUIT Measurements are from 10 fruit sampes | | |
| Fruit: overall size | medium 91 g | [large] |
| Fruit: mean length | 73.9 mm (69.1–79.1 mm) | |
| Fruit: width (max.) | 51.56 mm (47.4–55.0 mm) | |
| Fruit: width (min.) | 44.9 mm 42.8–47.3 mm) | |
| Fruit: locule number | 36.9 (33–40) | |
| Fruit: general shape | ovoid (tapers toward stylar end) | |
| Fruit: cross-section at median | elliptical | [oblate] |
| Fruit: general shape of stylar end | raised | [flat] |
| Fruit: shape of shoulder on salk end | rounded | [almost square] |
| Fruit: skin color at harvest (fruit still hard) | reddish-brown | [brown] |
| Fruit: skin color change during ripening | absent | |
| Fruit: skin color at maturity for consumption | reddish-brown | [brown] |
| Fruit: hairs | present | |
| Fruit: density of hairs | medium | |
| Fruit: type of hair | bristly | [hirsute] |
| Fruit: concentration of hairs | uniform | |
| Fruit: adherenece of hairs to skin (when rubbed) | weak | [strong] |
| Fruit: core (columella) diameter (at largest dia.) | medium to large | [large] |
| Fruit: core shape (in cross section) | elliptical | |
| Fruit: core woody spike | present | |
| Fruit: prominence of core woody spike | medium | |
| Fruit: outer pericarp color at maturity for consumption | light green | |
| Fruit: inner pericarp color (locules) at maturity for consumption | green | |
| Fruit: core color at maturity | greenish white | |
| Fruit: soluble solids concentration SSC (Brix level) at maturity for consumption | medium - 14.3% (13.5–15.1%) | |
| Fruit: Vitamin C content at harvest | medium (100–125 mg/ 100 g fresh weight) | |
| Fruit: seed color at maturity | dark brown | |
| Fruit: seed color when dry | brown | |

-continued

TABLE OF CHARACTERISITCS
Characters of the 'Hayward' comparison cultivar are noted in [bracket] opposite that character only when significantly different.
All dimensions in millimeters, weights in grams.

| | Tomua | Hayward |
|---|---|---|
| EVENTS (at Te Puke, New Zealand) | | |
| Time of vegetative budbreak | early (late August to first week of Sept.) | |
| Time of beginning of flowering | medium (second) to third week of Sept.) | [two weeks later] |
| Time of harvest at 6.2% SSC | medium (first weak of April) | [four weeks later] |

HORTICULTURAL CHARACTERISTICS

Details below relate to observations made on plants grafted on 'Hayward' clonal rootstocks (rooted cuttings) growing at Te Puke Research Centre, New Zealand.

'Tomua' vines can be grown on the same rootstocks as can 'Hayward' vines. Rootstocks currently used in New Zealand include *A. deliciosa* seedlings, 'Hayward' rooted cuttings and Hortkiwi 'Kaimai'. 'Tomua' can also be grown as self-rooted cutting grown plants.

In Te Puke, from 1993–1997 the 'Tomua' harvest time has been consistently 4–5 weeks ahead of 'Hayward' using the criteria of a Soluble Solids Concentration (SSC) of 6.2% to begin harvest.

The storage life of 'Tomua' fruit is about half of that of 'Hayward' fruit under cool storage temperatures of 0° C., but this is not considered a disadvantage as 'Tomua' fruit can be sold before the main 'Hayward' crop is harvested.

'Tomua' fruit soften more rapidly than 'Hayward' fruit so the consumer can more readily obtain fruit that is in a "ready-to-eat" condition at the start of the kiwi fruit harvest season. 'Tomua' fruit are sweeter tasting than 'Hayward' with a tangy balance of sweetness and acidity.

Yield data: 'Tomua' vines carry lower yields of Class 1 (export grade) fruit than 'Hayward' when plants of equivalent ages are compared, mainly because fruit of 'Tomua' are smaller on average than those of 'Hayward'.

Three years of data from a replicated trial planting containing 'Tomua' and 'Hayward', planted in 1989 at Te Puke is presented below in Table 1.

TABLE 1

TOMUA AND HAYWARD YIELDS

| | Fruit number | | Trays (3.6 kg) | | Size (grams) | |
|---|---|---|---|---|---|---|
| Year | Tomua | Hayward | Tomua | Hayward | Tomua | Hayward |
| 1996 | 938 | 708 | 23 | 22 | 92 | 117 |
| 1997 | 909 | 1331 | 23 | 35 | 93 | 96 |
| 1998 | 1149 | 1020 | 24 | 30 | 89 | 111 |
| Means | 999 | 1020 | 23 | 29 | 91 | 108 |

Fruit flesh and skin color measurement.
RHS Colour Chart, the Royal Horticultural Society, London 1966.

TABLE 1-continued

| | | |
|---|---|---|
| Flesh Color at maturity: | | |
| Outer pericarp | 138B–138D | [Hayward 138B–138C] |
| Tomua | | |
| Fruit core: | | |
| Tomua | 155–155B | [Hayward 155A] |
| Seed color (in fruit): | 200A | |
| Seed color (dry seed): | 165A–165B | |
| Fruit skin at maturity: | | |
| Tomua | 165B | [Hayward 164B] |
| Leaf color: mature leaf after petal fall | | |
| Upper side of leaf | 137A or | |
| Tomua | 147A | |
| Lower side of leaf | 147B–147C | |

TABLE 1-continued

| | |
|---|---|
| Tomua | |
| Petiole color: | |
| exposed side | 178B |
| Flower petals: | |
| main body | 155D |
| base | 154C–154D |
| Plant Stem: | |
| exposed side: | 165A |
| Lenticel color: | 164B–164C. |

We claim:

1. A new and distinct kiwi plant of the species *A. deliciosa* substantially as described and illustrated in the specification above, characterised by early harvest date compared to 'Hayward', medium green flesh, reddish-brown skin, easily removable hairs, and a slight pointed stylar end.

* * * * *